US009124214B2

United States Patent
Haunschild et al.

(10) Patent No.: US 9,124,214 B2
(45) Date of Patent: Sep. 1, 2015

(54) METHOD FOR SPATIALLY DETERMINING THE SERIES RESISTANCE OF A SEMICONDUCTOR STRUCTURE

(75) Inventors: Jonas Haunschild, Freiburg (DE);
Markus Glatthaar, Freiburg (DE);
Stefan Rein, Denzlingen (DE)

(73) Assignees: Fraunhofer-Gesellschaft Zur Förderung Der Angewandten Forschung E.V., München (DE);
Albert-Ludwigs-Universität Freiburg, Freiburg (DE)

( * ) Notice: Subject to any disclaimer, the term of this patent is extended or adjusted under 35 U.S.C. 154(b) by 952 days.

(21) Appl. No.: 13/321,404

(22) PCT Filed: May 17, 2010

(86) PCT No.: PCT/EP2010/002997
§ 371 (c)(1),
(2), (4) Date: Jan. 24, 2012

(87) PCT Pub. No.: WO2010/133325
PCT Pub. Date: Nov. 25, 2010

(65) Prior Publication Data
US 2012/0113415 A1    May 10, 2012

(30) Foreign Application Priority Data

May 18, 2009 (DE) .......................... 10 2009 021 799

(51) Int. Cl.
*G01J 1/02* (2006.01)
*G01J 3/50* (2006.01)
(Continued)

(52) U.S. Cl.
CPC ............ *H02S 50/10* (2014.12); *G01N 21/6489* (2013.01); *G01N 21/66* (2013.01)

(58) Field of Classification Search
CPC ................. G01J 3/50; G01J 1/02; H02S 50/10
USPC ................................................ 362/458.1, 362
See application file for complete search history.

(56) References Cited

U.S. PATENT DOCUMENTS

2010/0025588 A1 * 2/2010 Trupke et al. ................. 250/362

FOREIGN PATENT DOCUMENTS

WO    2007128060    11/2007

OTHER PUBLICATIONS

Trupke, T. et al., "Spatially Resolved Series Resistance of Silicon Solar Cells Obtained from Luminescence Imaging", Applied Physics Letters 90, 093506 (2007).
(Continued)

*Primary Examiner* — David Porta
*Assistant Examiner* — Faye Boosalis
(74) *Attorney, Agent, or Firm* — Volpe and Koenig, P.C.

(57) ABSTRACT

A method for spatially determining the series resistance of a semiconductor structure by generating luminescent radiation in the semiconductor structure under measurement conditions A and B, by determining a local calibration parameter $C_{V,i}$ for a plurality of prescribed locations of the semiconductor structure and determining local series resistances $R_{S,i}$ for a plurality of prescribed locations of the semiconductor structure. It is essential that the local series resistances $R_{S,i}$ are each determined as a function of a global series resistance $R_{Sg}$ of the semiconductor structure that is identical for all local series resistances.

10 Claims, 1 Drawing Sheet

(51) Int. Cl.
*H02S 50/10* (2014.01)
*G01N 21/64* (2006.01)
*G01N 21/66* (2006.01)

(56) References Cited

OTHER PUBLICATIONS

Kampwerth, H., et al. "Advanced Luminescence Based Effective Series Resistance Imaging of Silicon Solar Cells", Applied Physics Letters 93, 202102 (2008).

Psych, D., et al. "A Review and Comparison of Different Methods to Determine the Series Resistance of Solar Cells", Solar Energy Materials & Solar Cells 91 (2007), pp. 1698-1706.

Ramspeck, K., et al. "Recombination Current and Series Resistance Imaging of Solar Cells by Combined Luminescence and Lock-in Thermography", Applied Physics Letters 90, 153502 (2007).

Michl, B., et al. "Application of Luminescence Imaging Based Series Resistance Measurement Methods in an Industrial Environment", Proceedings of the 23rd European Photovoltaic Solar Energy Conference and Exhibition, Sep. 5, 2008, pp. 1-6.

* cited by examiner

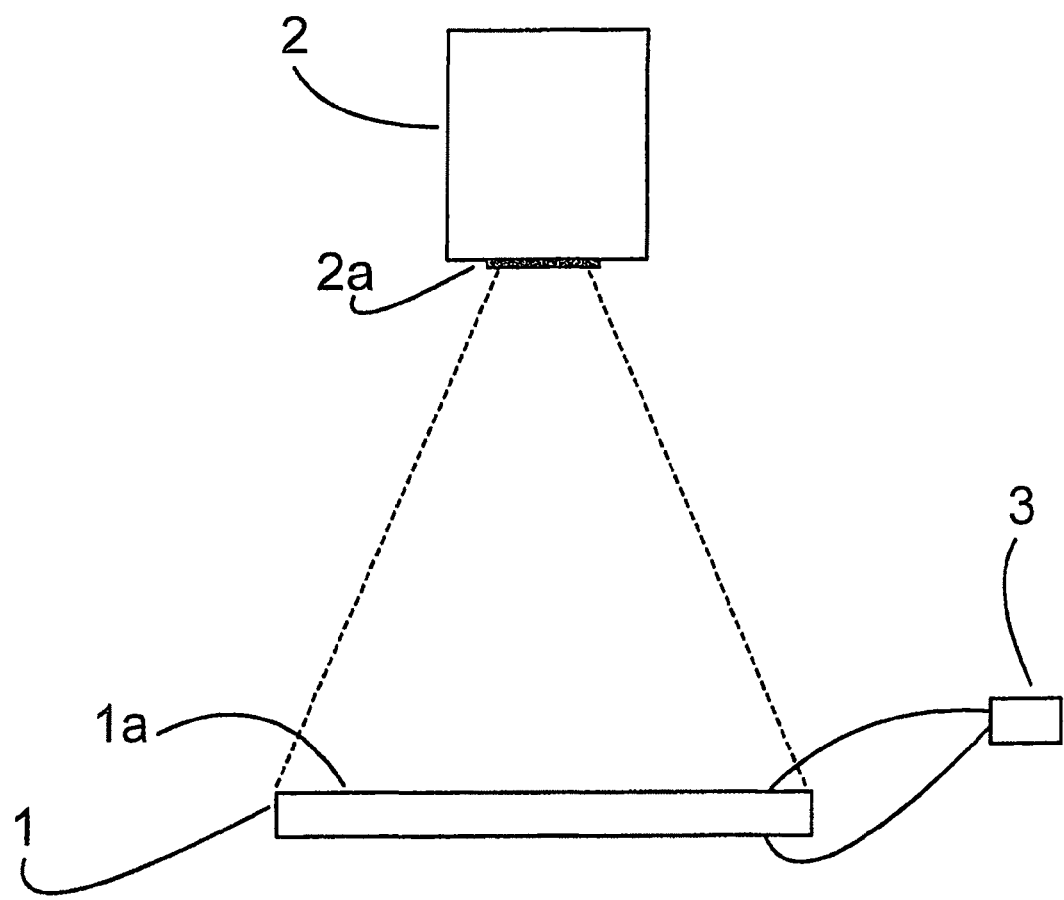

METHOD FOR SPATIALLY DETERMINING THE SERIES RESISTANCE OF A SEMICONDUCTOR STRUCTURE

BACKGROUND

The present invention relates to a method for the spatially resolved determination of the series resistance of a semiconductor structure as recited in the preamble of Claim 1, the semiconductor structure being a solar cell or a preliminary stage in the production of a solar cell, including at least one pn junction and contacts for electrical contacting.

The series resistance is an essential quantity for characterizing a solar cell, because a high series resistance typically causes a reduction of the efficiency of the solar cell. The total series resistance of a solar cell is comprised of a plurality of portions; for example, the cross-conductor resistance of a metallic contacting structure, the cross-conductor resistance of a doping layer such as an emitter layer, and/or the contact resistance between the metallic contact structure and the doping layer can contribute essentially to the total series resistance.

In order to characterize a solar cell, as well as for process control in the production of a solar cell, it is desirable to determine the series resistance of the solar cell in spatially resolved fashion, i.e. to determine the local series resistance at each of a plurality of locations. The distribution of the local series resistances enables inferences to be drawn concerning locally inhomogenous process conditions, or faulty elements such as interrupted metallization structures.

A number of measurement methods are known for the spatially resolved determination of the series resistance; in particular, the spatially resolved measurement of luminescence radiation produced in the solar cell is suitable for such measurement methods. It is already known to use a CCD camera to measure, in spatially resolved fashion, the luminescence radiation emanating from a surface of the solar cell, and on this basis to determine the series resistance in spatially resolved fashion:

In T. Trupke, E. Pink, R. A. Bardos, and M. D. Abbott, *"Spatially resolved series resistance of silicon solar cells obtained from luminescence imaging," Applied Physics Letters* 90, 093506 (2007), a method is described in which luminescence radiation is produced by illuminating the solar cell in a known manner, and this so-called photoluminescence radiation is measured in spatially resolved fashion using a CCD camera. Here, two images of the photoluminescence radiation are taken under different measurement conditions; under one measurement condition A, open-circuit conditions are present (i.e., there is no flow of current between the contacts), and under a measurement condition B current is drawn from the solar cell. In addition, at least one third image of the photoluminescence radiation under short-circuit conditions is required in order to clear the measurement values of the two previously noted images.

From the measurement image taken under measurement condition A, spatially resolved calibration parameters $C_i$ are determined, one calibration parameter being determined for each location i. Using these calibration parameters, the local intensities of the luminescence radiation, measured under measurement condition B, are converted into a voltage present locally at the respective location of the solar cell.

Under the assumption that a uniform value for a dark saturation current can be assumed for the entire solar cell, the determination of the local series resistances is possible using the known one-diode model as an approximation for the modeling of the local electrical properties of the solar cell.

In typical commercially produced solar cells, in particular solar cells made of multicrystalline silicon, however, a locally homogenous dark saturation current cannot be assumed. For the quantitative determination of the local series resistances in such solar cells, a spatially resolved determination of the dark saturation current is therefore additionally required.

Standardly, for this purpose further measurements of the photoluminescence are necessary under different measurement conditions, such as exposing the solar cell to electromagnetic radiation having different wavelengths.

SUMMARY

The present invention is therefore based on the object of improving the measurement method for spatially resolved determination of the series resistance of a semiconductor structure in such a way that the number of required measurement images is reduced and/or the required overall duration for the spatially resolved determination of the series resistance is reduced. In addition, the measurement method according to the present invention should be suitable for use in in-line measurement stations in a production line for solar cells.

This object is achieved by a method for spatially resolved determination of the series resistance of a semiconductor structure according to the invention. Advantageous embodiments of the method according to the present invention are found in the description that follows and the Claims.

Using the method according to the present invention, spatially resolved series resistances of a semiconductor structure are determined, the semiconductor structure being a solar cell or a preliminary stage in the production of a solar cell. The semiconductor structure includes at least one pn junction and contacts for electrical contacting.

The method includes the following method steps:

In a step A, luminescence radiation is produced in the semiconductor structure under a measurement condition A, an electrical voltage $V_A$ being present between the contacts of the semiconductor structure. For a plurality of locations i of the semiconductor structure, the local intensity $I_{LA,i}$ of the luminescence radiation emanating from this location is measured.

In a step B, luminescence radiation is produced in the semiconductor structure under a measurement condition B, an electrical voltage $V_B$ being present between the contacts of the semiconductor structure. The measurement condition B differs from measurement condition A in that under measurement condition B a larger current flows between the contacts of the semiconductor structure than is the case under measurement condition A. Analogous to step A, in step B there also takes place, for each of a plurality of locations, a measurement of the respective local intensity $I_{LB,i}$ of the luminescence radiation emanating from this location of the semiconductor structure.

In a step C, for each of a plurality of specified locations of the semiconductor structure a respective local calibration parameter $C_{V,i}$ is determined for a specified mathematical relation between the local intensity of the luminescence radiation and the voltage locally present at the semiconductor element at the respective location. The determination of calibration parameters $C_{V,i}$ here takes place at least as a function of the intensities $V_{LA,i}$ determined in step A and the voltage $V_A$ existing between the contacts of the semiconductor structure under measurement condition A.

Finally, in a step D there takes place the determination of local series resistances $R_{S,i}$ for a plurality of specified locations of the semiconductor structure. The determination takes place in each case at least as a function of at least one local intensity $I_{LB,i}$ of the luminescence radiation, measured in step B, and at least one calibration parameter $C_{V,i}$ determined in step C.

It is essential that in step D the local series resistances $R_{S,i}$ are each additionally determined as a function of a global series resistance $R_{Sg}$ identically specified for all local series resistances, of the semiconductor structure.

In contrast to the previously known measurement methods, in which additional measurements of the luminescence radiation are necessary for the determination of the local series resistances in step D, in the measurement method according to the present invention the global series resistance of the semiconductor structure is additionally used to determine the local series resistances. This makes possible a reduction of the necessary measurements of the luminescence radiation, and a corresponding reduction of the measurement duration required for the overall measurement.

This reduction makes it possible in particular to use the method according to the present invention in already-existing in-line measurement devices, in which a measurement of the semiconductor structure takes place during the production process.

In the measurement method according to the present invention, the required additional information in step D for determining the local series resistances is thus obtained not via additional measurements of the luminescence radiation, but rather through a specified global series resistance of the semiconductor structure. The global series resistance of the semiconductor structure is comparatively easy to determine. For this purpose, a variety of measurement methods known from the prior art are available:

For example, the series resistance can be determined from the dark or bright characteristic of the semiconductor structure, or from a combination of the dark and bright characteristic of the semiconductor structure, in a known manner (see D. Pysch, A. Mette, and S. W. Glunz, Solar Energy Materials & Solar Cells 91, 1698-706 (2007), and A. G. Aberle, S. R. Wenham, and M. A. Green, in *A new method for accurate measurements of the lumped series resistance of solar cells*, Louisville, Ky., USA, 1993 (IEEE; New York, N.Y., USA), pp. 133-9). It is also possible to calculate the global series resistance on the basis of characteristic data of the semiconductor structure, such as size dimensions of the metallization structures, size dimensions of the doping layers, and doping profiles or layer resistances of the doping layers.

A further advantage of the use of the global series resistance for the determination of the local series resistances is that in a process line the fluctuation of the global series resistance between the individual semiconductor structures is typically significantly less than the fluctuation of the local series resistances on one semiconductor structure. It is thus not necessarily required to determine the global series resistance individually for each semiconductor structure. It is also possible to use a global series resistance that is typical for the semiconductor structure.

Investigations on the part of applicant have shown that, advantageously, the determination of the local series resistances takes place as a function of the global series resistance in such a way that the local series resistances $R_{S,i}$ are each scaled with a global scaling factor f that is identical for all local series resistances. The global scaling factor f is determined in such a way that the local series resistances $R_{S,i}$ have a specified mathematical relation to the global series resistance $R_{Sg}$.

This specified mathematical relation is preferably a specified averaging method over the local series resistances $R_{S,i}$, so that the resulting mean value of the scaled local series resistances $R_{S,i}$ is equal to the global series resistance $R_{Sg}$. Investigations on the part of applicant have shown that arithmetic averaging is preferably used as the averaging process.

The method according to the present invention is usable both in the case of the production of luminescence radiation by providing the semiconductor structure with electromagnetic radiation (i.e. production of photoluminescence radiation) and in the case of production of the luminescence radiation through application of a voltage to the contacts of the semiconductor structure (i.e. production of electroluminescence radiation).

In the case of the production of photoluminescence radiation, for example under measurement condition A, contacting of the semiconductor structure can be omitted. In this case, the voltage $V_A$ applied to the contacts results from the illumination conditions, and no current flows between the contacts. In the case of measurement condition B, a contacting is necessary in order to produce a specified flow of current between the contacts for a correspondingly present voltage $V_B$. In this case as well, under measurement condition B there thus flows a larger current than under measurement condition A. However, given the production of photoluminescence radiation there arises the disadvantage that the electromagnetic radiation used for the excitation must not be detected as photoluminescence radiation, so that expensive optical filters are required to screen out the excitation radiation at the detection unit used, such as a CCD camera. In the embodiment of the method as an electroluminescence method, such optical filters can be omitted.

Advantageously, therefore, under measurement condition A the semiconductor structure is supplied with voltage $V_A$ at the electrical contacts, and under measurement condition B with the voltage $V_B$. Under both these measurement conditions, the semiconductor structure is not supplied, or is supplied only slightly, with electromagnetic radiation. Preferably, the measurement thus takes place in the dark. However, a slight illumination of the semiconductor structure is also possible as long as the measurement conditions, i.e. in particular the charge carrier distribution in the semiconductor structure, are essentially determined by the present voltage and not by the illumination.

In the advantageous embodiment of the method according to the present invention as an electroluminescence method, $V_A$ is smaller than $V_B$, so that under measurement condition A a smaller current flows between the contacts of the semiconductor structure, compared to measurement condition B.

The background of this is that under measurement condition A the influence of the local series resistances on the current flow pattern in the semiconductor structure must be kept as small as possible. This is because, as described above, the measurement of the luminescence radiation under measurement condition A is used to determine the local calibration parameters $C_{V,i}$, and it is desirable that there be no influence, or only a slight influence, of the local series resistances on the determined calibration parameters.

Likewise, however, a low electrical voltage $V_A$, and correspondingly a low flow of current, between the contacts of the semiconductor structure under measurement condition A results in lower intensities of the local luminescence radiation compared to measurement condition B. Measurement condition A is therefore advantageously selected such that on the one hand the influence of the local series resistances is low, but on the other hand an intensity of the produced luminescence radiation is achieved that is as large as possible, in order to keep the necessary measurement time for spatially resolved detection of the luminescence radiation short.

Preferably, under measurement condition A a current therefore flows between the contacts of the semiconductor structure that is less than 30%, preferably less than 20%, further preferably less than 15% of the current that flows under normal operation of the semiconductor structure.

"Normal operation" here designates the standard test condition for which the semiconductor structure is fashioned. In standard commercially available solar cells for outdoor use, this typically means a supplying to the solar cell of electromagnetic radiation having the normal spectrum AM1.5G, with an overall power of 1000 W/m² of illuminated surface. Investigations on the part of applicant have shown that a measurement condition A, under which there flows approximately 20% of the short-circuit current under normal conditions, brings about a good optimization between low influence of the local series resistances on the one hand and high intensity of the produced luminescence radiation on the other hand.

In the case of measurement condition B, in contrast, it is necessary for the influence of the local series resistances to be apparent in the produced luminescence radiation. Therefore, under measurement condition B there advantageously flows a current between the contacts of the semiconductor structure that is at least 50%, preferably at least 70%, further preferably approximately 100% of the short-circuit current that flows under normal conditions of the semiconductor structure. In particular, it is advantageous if the open-circuit voltage under normal conditions ($V_{OC}$) is applied to the semiconductor structure under measurement condition B.

As described above, the intensity of the produced luminescence radiation under measurement condition A is less than under measurement condition B. Advantageously, the measurement time for the spatially resolved measurement of the luminescence radiation is therefore greater in step A by at least approximately a factor of three, preferably approximately a factor of five, than the measurement time for the measurement of the intensity of the luminescence radiation in step B.

With typical semiconductor solar cells, in particular solar cells made of multicrystalline silicon, and with the use of a standard CCD camera for the detection of the luminescence radiation, under measurement condition A a measurement duration of less than 0.5 seconds is possible, and under measurement condition B a measurement duration of less than 0.1 seconds is possible.

The relation between the voltage locally present at the semiconductor structure and the luminescence radiation locally produced by this present voltage can be described approximately as an exponential relation. Advantageously, in step C an exponential relation is therefore specified between the intensity of the local luminescence radiation $I_{LA,i}$ and the voltage $V_A$, in particular preferably according to equation 1:

$$I_{LA,i} = C_{V,i} \exp\left(\frac{V_A}{V_T}\right), \quad \text{(Equation 1)}$$

with the local calibration parameter $C_{V,i}$ and the thermal voltage $V_T$ to be determined in step C.

In this advantageous embodiment, using the local calibration parameter it is therefore possible to convert the intensity of the measured luminescence radiation into a locally present voltage.

Advantageously, in step D each local series resistance is determined according to equation 2:

$$R_{S,i} = \frac{V_B - V_i}{j_i}, \quad \text{(Equation 2)}$$

with a local voltage $V_i$ present at the semiconductor structure and a local current density $j_i$ flowing in this region of the semiconductor structure. Here, the local voltage is a function at least of the local intensity $I_{B,i}$ measured in step B and the local calibration parameters $C_{V,i}$ determined in step B, preferably according to the above-named Equation 1.

The local current density $j_i$ is preferably determined according to Equation 3:

$$j_i = j_{0,i} \exp\left(\frac{V_i}{V_T}\right) \quad \text{(Equation 3)}$$

with the local voltage $V_i$, the thermal voltage $V_T$, and the local dark saturation current density $j_{0,i}$.

The local dark saturation current density $j_{0,i}$ is preferably determined according to Equation 4:

$$j_{0,i} = \frac{f}{C_{V,i}} \quad \text{(Equation 4)}$$

with the local calibration parameter $C_{V,i}$ and the above-named global scaling factor f. The global scaling factor f is here determined in such a way that the local series resistances $R_{S,i}$ have a specified mathematical relation to the global series resistance $R_{Sg}$, preferably such that the arithmetic mean of the scaled local series resistances corresponds to the global series resistance.

In this preferred embodiment, there thus takes place a scaling of the local series resistances via a scaling of the local dark saturation current densities, under the condition that the arithmetic mean of the local series resistances corresponds to the global series resistance. Due to this scaling, further measurements can be done without, in particular further measurements of the spatially resolved luminescence radiation for the quantitative determination of the local series resistances.

In the embodiment of the method according to the present invention as an electroluminescence method, the determination of the local series resistances is thus quantitatively possible, requiring only one measurement of the local luminescence radiation under each of two measurement conditions, as well as the specification of a global series resistance of the semiconductor structure.

In order to increase the measurement precision, it is advantageous that in step A at least one production of luminescence radiation additionally takes place in the semiconductor structure under a second measurement condition A' in which an electrical voltage $V_A'$ exists between the contacts of the semiconductor structure, and for each of a plurality of locations of the semiconductor structure a local intensity $I_{LA,i}'$ of the luminescence radiation emanating from this location is measured. Under measurement condition A', a current flows between the contacts of the semiconductor structure that differs from that flowing under measurement condition A, and in step C an exponential relation is specified between the intensity of the local luminescence radiation $I_{LA,i}$ and the voltage $V_A$, according to Equation 5:

$$I_{LA,i} = C_{V,i} \exp\left(\frac{V_A}{m_{V,i} \cdot V_T}\right), \quad \text{(Equation 5)}$$

with thermal voltage $V_T$ and local calibration parameters $C_{V,i}$ and $m_{V,i}$. Correspondingly, in step C the local calibration parameters $C_{V,i}$ and $m_{V,i}$ are determined as a function of the measured intensities $I_{LA,i}$ and $I_{LA,i}'$, and in step D the local series resistances $R_{S,i}$ are each additionally determined as a function of the local calibration parameter $m_{V,i}$.

In this preferred specific embodiment, a simpler exponential relation according to Equation 1 is therefore not assumed for the mathematical relation between the voltage locally present at the semiconductor structure and the intensity of the luminescence radiation produced in this region of the semiconductor structure; rather, an exponential relation is assumed that additionally has a local ideality factor $m_{V,i}$. Correspondingly, two measurements (a measurement under measurement condition A and a measurement under measurement condition A') are required of the intensities of the local luminescence radiation in order to determine the two calibration parameters for each location.

The additional expense of a further measurement increases the precision in the evaluation due to the additional calibration parameter $m_{V,i}$.

It also lies within the scope of the present invention to assume, for the mathematical relation between the intensity of the local luminescence radiation and the locally present voltage, additional mathematical models having additional calibration parameters, and correspondingly to carry out in step A additional measurements of the local luminescence intensities under further measurement conditions, in order also to determine the further calibration parameters.

Investigations on the part of applicant have, however, shown that with the use of Equation 1, i.e. the determination only of a local calibration parameter $C_{V,i}$ for each location, a sufficient degree of precision is already achieved for typical semiconductor structures.

Preferably, the same locations are specified in each of steps A, B, C, and D. In this way, for each specified location i an intensity $I_{LA,i}$, an intensity $I_{LB,i}$, a local calibration parameter $C_{V,i}$, and correspondingly a local series resistance $R_{S,i}$ are determined, the determination for each location of the local series resistance being independent of the corresponding measurement values or parameters of the other locations. However, it also lies within the scope of the present invention to specify different locations for individual method steps, and during the evaluation in step D to carry out, for each location for which a local series resistance $R_{S,i}$ is to be determined, an averaging of the measurement values or calibration parameters measured in the environment of this location.

Preferably, the specified locations are distributed approximately uniformly over a surface of the semiconductor structure, preferably the front side of the semiconductor structure.

In particular given the use of CCD cameras for measuring the luminescence radiation, cameras are advantageously used that have a chip having a quadratic or rectangular raster of pixels, such that a location on measurement side 1a is allocated to each pixel via an objective, and thus the specified locations are also situated on a rectangular or quadratic raster on the semiconductor structure.

Preferably, the execution of the method according to the present invention takes place at a large number of locations in order to obtain spatially sufficiently resolved information regarding the local series resistances. Preferably, method steps B, C, and D are carried out for at least 1000, preferably at least 20,000, further preferably at least 100,000 different locations. The locations preferably have a distance from one another of at least 0.1 mm, preferably at least 0.3 mm, preferably at least 1 mm. Preferably, the locations are situated on a rectangular grid, preferably a quadratic grid. As described above, the use of a CCD camera is in particular advantageous. Preferably, all measurement points of the camera are used in order to carry out method steps B, C, and D. Typical CCD cameras have a resolution of at least 250,000 pixels, situated on a quadratic grid (at least 512 pixels×512 pixels). Preferably, the locations are selected such that representative regions with regard to the local series resistance of the solar cell are covered by the selected locations. In particular, it is advantageous to omit regions covered by contacting structures, such as metallization lines or metallization grids, in the selection of the locations.

The method according to the present invention is suitable in particular for silicon solar cells in which, due to the material parameters and process parameters, a locally inhomogenous dark saturation current density is present, such as for example solar cells made of multi-crystalline silicon.

The above-named physical quantities have the following units:
a. Electrical voltages $V_A$, $V_B$: [V]
b. Local intensities $I_{LA,i}$, $I_{LB,i}$, and $I_{LA,i}$ of the luminescence radiation: [1]
c. Calibration parameter $C_{V,i}$: [1]
d. Scaling factor f: [A/m²]
e. Calibration parameter $m_{V,i}$: [1]
f. Current densities $j_i$, $j_{0,i}$: [A/m²]

BRIEF DESCRIPTION OF THE DRAWINGS

Further features and preferred embodiments of the method according to the present invention are explained in the following on the basis of an exemplary embodiment and FIG. 1.

FIG. 1 shows a schematic representation of a measuring system for the realization of an exemplary embodiment of the method according to the present invention.

DETAILED DESCRIPTION OF THE PREFERRED EMBODIMENTS

A multicrystalline silicon solar cell 1 has on its front side 1a a grid-type metallic contacting structure, and has on its opposite, rear side a whole-surface rear side contact. Through the use of a controllable voltage source 3, a voltage is specified between the front and rear side contact of solar cell 1 in order to produce electroluminescence radiation.

The electroluminescence radiation emanating from front side 1a of solar cell 1 is measured in spatially resolved fashion by a CCD camera 2. CCD camera 2 includes a CCD chip having a quadratic raster of pixels, a location on front side 1a of solar cell 1 being allocated to each pixel via an objective 2a.

The measuring system further includes a control and evaluation unit (not shown) that is connected to CCD camera 2 and to voltage source 3.

The entire measurement process takes place in the dark. First, a measurement condition A is produced in which an electrical voltage $V_A$ is applied between the front and rear side contact of solar cell 1. Solar cell 1 is a multicrystalline silicon solar cell having an open-circuit voltage of 620 mV. Voltage $V_A$ is 570 mV, and is selected such that approximately 20% of the short-circuit current under normal conditions flows between the front and rear contact. In this way, it is ensured that, under measurement condition A, on the one hand the influence of the local series resistances is negligible, and on the other hand a sufficiently high intensity is achieved of the produced electroluminescence radiation, so that, with a measurement time of approximately 0.25 seconds, a sufficiently noise-free measurement image of the spatially resolved luminescence radiation is recorded by CCD camera 2 in order to measure local intensities $I_{LA,i}$.

Subsequently, a measurement condition B is produced in which voltage source 3 is used to apply an electrical voltage to the contacts of the solar cell, said voltage corresponding to open-circuit voltage $V_{OC}$ of the solar cell (for the multicrystalline silicon solar cell used in this exemplary embodiment, $V_{oc}$=approx. 620 mV). At this voltage, approximately the short-circuit current under normal conditions flows between the contacts of solar cell 1, so that under measurement condition B there is a significant influence of the local series resistances.

Under measurement condition B, CCD camera 2 is used to record a measurement image of the local intensities $I_{LB,i}$ of the luminescence radiation emanating from the solar cell. Because under measurement condition B a greater current flows in comparison to measurement condition A, and correspondingly the intensities of the luminescence radiation are also greater, here a measurement time of 0.05 seconds is sufficient.

Because the solar cell does not move relative to CCD camera 2 during the measurements, the locations of the respective measurements are also identical.

Correspondingly, in a step C a local calibration parameter $C_{V,i}$ is determined according to Equation 1 for each of the measured locations. For each location i, the local calibration parameter $C_{V,i}$ is determined for this location using the electrical voltage $V_A$ applied under measurement condition A and using the intensity, determined for this location, of the luminescence radiation. The thermal voltage $V_T$=kT/q (with Boltzmann constant k and elementary charge q) is here given via the temperature T present during the measurement, i.e. typically the ambient temperature of the measuring system. Preferably, the measurement environment is tempered to approximately 25° C.

Subsequently, the local series resistance is calculated according to Equation 2 for each location i.

For this purpose, first the local voltage $V_i$ is determined by solving Equation 1 for $V_i$:

$$V_i = V_T \cdot \ln\left(\frac{I_{LB,i}}{C_{V,i}}\right) \quad \text{(Equation 6)}$$

with thermal voltage $V_T$, intensity $I_{B,i}$ of the luminescence radiation, measured for this location under measurement condition B, and local calibration parameter $C_{V,i}$ determined for this location.

The local current density $j_i$ is determined for each location according to Equation 3, with the local voltage $V_i$ determined as described above and with a local dark saturation current density $j_{0,i}$.

The local dark saturation current density is determined according to Equation 4 with the local calibration parameter $C_{V,i}$ and the global scaling factor f.

The global scaling factor f is in turn determined such that the mean value of the local series resistances corresponds in its arithmetic mean to the specified global series resistance:

$$f = \frac{1}{R_{Sg}} \frac{1}{N} \sum_{i=1}^{N} \frac{V_i - V_B}{C_{V,i}^{-1} \exp(V_i/V_T)} \quad \text{(Equation 7)}$$

with the total number N of specified locations, the specified global series resistance $R_{Sg}$, the local voltage $V_i$, calculated for each location i as described above, the voltage $V_B$ applied to the contacts of the solar cell under measurement condition B, the local calibration parameter $C_{V,i}$ determined for each location i, and the thermal voltage $V_T$.

Here, the global series resistance $R_{Sg}$ of solar cell 1 was previously determined by measuring and comparing bright and dark characteristics of solar cell 1 and determining the global series resistance in a known manner (as described in A. G. Aberle, S. R. Wenham, and M. A. Green, *A new method for accurate measurements of the lumped series resistance of solar cells*, Louisville, Ky., USA, 1993 (IEEE; New York, N.Y., USA), pp. 133-9).

The invention claimed is:

1. A method for spatially resolved determination of a series resistance of a semiconductor structure, which is a solar cell (1) or a preliminary stage of a solar cell (1), comprising at least one pn junction and contacts for electrical contacting of the semiconductor structure, the method comprising the following method steps:

A producing luminescence radiation in the semiconductor structure under a measurement condition A, in which an electrical voltage $V_A$ exists between contacts of the semiconductor structure, and, for each of a plurality of locations of the semiconductor structure, measuring a local intensity $I_{LA,i}$ of a luminescence radiation emanating from this location, B producing luminescence radiation in the semiconductor structure under a measurement condition B in which an electrical voltage $V_B$ exists between the contacts of the semiconductor structure, and, for each of the plurality of locations, measuring local intensities $I_{LB,i}$ of a luminescence radiation emanating from this location, with a larger current flowing between the contacts of the semiconductor structure under measurement condition B than under measurement condition A, C determining, for the plurality of the specified locations of the semiconductor structure, a local calibration parameter $C_{V,i}$ for a specified mathematical relation between the local intensity of the luminescence radiation and the voltage locally present at the location on the semiconductor element, the determination of the local calibration parameters $C_{V,i}$ taking place at least as a function of the intensities $I_{LA,i}$ of the luminescence radiation measured in step A and the voltage $V_A$ existing between the contacts of the semiconductor structure under measurement condition A, D determining a local series resistances $R_{S,i}$ for the plurality of the specified locations of the semiconductor structure, in each case at least as a function of at least one local intensity $I_{LB,i}$ of the luminescence radiation measured in step B and at least one local calibration parameter $C_{V,i}$ determined in step C, and in step D, the local series resistances $R_{S,i}$ are each additionally determined as a function of a global series resistance $R_{Sg}$ of the semiconductor structure that is identically specified for all of the local series resistances, wherein the local series resistances $R_{S,i}$ are each scaled with a global scaling factor f that is identical for all the local series resistances, the global scaling factor f being determined such that the local series resistances $R_{S,i}$ have a specified mathematical relation to the global series resistance $R_{Sg}$.

2. The method as recited in claim 1, wherein
the global scaling factor f is determined such that a specified averaging of the local series resistances $R_{S,i}$ is equal to the global series resistance $R_{Sg}$.

3. The method as recited in claim 1, wherein
under the measurement condition A, the semiconductor structure is supplied at the electrical contacts with the voltage $V_A$, and under the measurement condition B it is supplied at the electrical contacts with the voltage $V_B$, and under both measurement conditions the semiconductor structure is not supplied, or is supplied only slightly, with electromagnetic radiation, so that current flowing in the semiconductor structure is essentially caused by the respectively present voltage, and
that $V_A$ is smaller than $V_B$.

4. The method as recited in claim 3, wherein
during the measurement of the intensity $I_{LA}$ in step A, a measurement time is greater at least by a factor of three, preferably by approximately a factor of five, than a measurement time during the measurement of the intensity $I_{LB}$ in step B.

5. The method as recited in claim 4, wherein
under the measurement condition A, a current flows between the contacts of the semiconductor structure that is less than 30% of a short-circuit current flowing under normal conditions of the semiconductor structure.

6. The method as recited in claim 5, wherein
under measurement condition B, a current flows between the contacts of the semiconductor structure that is at least 50% of the short-circuit current flowing under the normal condition of the semiconductor structure.

7. The method as recited in claim 1, wherein
in step C an exponential relation is specified between an intensity of the local luminescence radiation $I_{LA,i}$ and the voltage $V_A$,
according to Equation 1:

$$I_{LA,i} = C_{V,i} \exp\left(\frac{V_A}{V_T}\right), \quad \text{(Equation 1)}$$

with a local calibration parameter $C_{V,i}$ that is to be determined in step C, and with a thermal voltage $V_T$.

8. The method as recited in claim 1, wherein
in step D each of the local series resistances is determined according to Equation 2:

$$R_{S,i} = \frac{V_B - V_i}{j_i}, \quad \text{(Equation 2)}$$

with a local voltage $V_i$ and a local current density $j_i$, the local voltage being a function at least of the local intensity $I_{B,i}$ measured in step B and the local calibration parameter $C_{V,i}$ determined in step B, and the local current density $j_i$ being determined according to Equation 3:

$$j_i = j_{0,i} \exp\left(\frac{V_i}{V_T}\right), \quad \text{(Equation 3)}$$

with the local voltage $V_i$, a thermal voltage $V_T$, and a local dark saturation current density $j_{0,i}$.

9. The method as recited in claim 8, wherein
in step D, the local series resistances $R_{S,i}$ are each scaled with a global scaling factor f that is identical for all the local series resistances, the global scaling factor f being determined such that the local series resistances $R_{S,i}$ have a specified mathematical relation to the global series resistance $R_{Sg}$, and
a local dark saturation current density $j_{0,i}$ is determined according to Equation 4:

$$j_{0,i} = \frac{f}{C_{V,i}}, \quad \text{(Equation 4)}$$

with the local calibration parameter $C_{V,i}$ and the global scaling factor f.

10. The method as recited in claim 1, wherein
in step A there additionally takes place at least a production of luminescence radiation in the semiconductor structure under a second measurement condition A' in which there exists an electrical voltage $V_A'$ between the contacts of the semiconductor structure, and for each of the plurality of locations of the semiconductor structure a local intensity $I_{LA,i}'$ is measured of the luminescence radiation emanating from this location, a current flowing between the contacts of the semiconductor structure under measurement condition A' that differs from that flowing under measurement condition A, and
that in step C an exponential relation is specified between the intensity of the local luminescence radiation $I_{LA,i}$ and the voltage $V_A$, according to Equation 5:

$$I_{LA,i} = C_{V,i} \exp\left(\frac{V_A}{m_{V,i} \cdot V_T}\right), \quad \text{(Equation 5)}$$

with a thermal voltage $V_T$ and the local calibration parameters $C_{V,i}$ and a local calibration parameter $m_{V,i}$,
in step C the local calibration parameters $C_{V,i}$ and $m_{V,i}$ are determined as a function of the measured intensities $I_{LA,i}$ and $I_{LA,i}'$, and
in step D the local series resistances $R_{S,i}$ are each additionally determined as a function of the local calibration parameter $m_{V,i}$.

* * * * *